(12) United States Patent
Kobayashi et al.

(10) Patent No.: US 6,576,721 B2
(45) Date of Patent: Jun. 10, 2003

(54) PROCESS FOR PRODUCING LOW POLYMER OF ETHYLENE

(75) Inventors: Ryoichi Kobayashi, Chiba (JP); Shigeki Kura, Chiba (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 10/182,703

(22) PCT Filed: Dec. 21, 2001

(86) PCT No.: PCT/JP01/11244
§ 371 (c)(1),
(2), (4) Date: Aug. 7, 2002

(87) PCT Pub. No.: WO02/051777
PCT Pub. Date: Jul. 4, 2002

(65) Prior Publication Data
US 2003/0027947 A1 Feb. 6, 2003

(30) Foreign Application Priority Data

Dec. 26, 2000 (JP) .......................................... 2000-395053
Feb. 23, 2001 (JP) .......................................... 2001-48434

(51) Int. Cl.⁷ .............................. C08F 2/06; C07C 2/08
(52) U.S. Cl. ........................... 526/70; 526/67; 585/512; 585/520; 585/523
(58) Field of Search ................................. 585/512, 520, 585/523; 526/67, 70

(56) References Cited

U.S. PATENT DOCUMENTS 3,655,812 A * 4/1972 Langer, Jr. .............. 585/523 X
5,449,850 A  9/1995 Young et al.

FOREIGN PATENT DOCUMENTS

JP  6-32745  2/1994

OTHER PUBLICATIONS

Abstract and Translated Claims of JP 07–149672, published Jun. 13, 1995.*

* cited by examiner

Primary Examiner—Fred Teskin
(74) Attorney, Agent, or Firm—Oblon, Spivak, McClelland, Maier & Neustadt, P.C.

(57) ABSTRACT

There is disclosed a process for producing an ethylenic oligomer which comprises subjecting ethylene to oligomerization reaction in an organic solvent in the presence of a Ziegler based catalyst, and recyclingly using for the oligomerization reaction, the organic solvent separated by distilling the resultant oligomerization reaction product, wherein the water concentration in the oligomerization reaction system is at most 8 ppm by weight, or the concentration of olefins which have at least 3 carbon atoms and which are contained in the organic solvent to be recycled in the oligomerization reaction system is at most 2% by weight. The process of the present invention can maintain the catalytic activity of the catalyst at a high level.

14 Claims, 5 Drawing Sheets

PROCESS FOR PRODUCING LOW POLYMER OF ETHYLENE

TECHNICAL FIELD

The present invention relates to a process for producing an ethylenic oligomer. More particularly, the present invention is concerned with a process for producing an ethylenic oligomer which is capable of producing a high quality ethylenic oligomer having enhanced purity, and in which a Ziegler based catalyst can maintain a high catalytic activity, when producing an ethylenic oligomer which is useful as a starting material for high molecular polymers, plasticizers, surfactants and the like by the use of the foregoing catalyst.

BACKGROUND ART

An ethylenic oligomer is a useful substance which is widely used as a starting monomer material for olefin polymers, as a comonomer for a variety of high molecular polymers, as a starting material for plasticizers, surfactants and the like. Usually, the ethylenic oligomer is produced by oligomerizing ethylene as the starting material by the use of a Ziegler based catalyst. The production process generally comprises the step of oligomerization reaction, the step of recovering unreacted ethylene, the step of deactivating the catalyst and deashing and the step of fractionating the solvent used therein and ethylenic oligomer.

A production process in which a Ziegler based catalyst is used as a catalyst for oligomerization reaction involves a problem in that a large amount of water, when being mixed in the reaction system, brings about partial deactivation of the catalyst, which as a result, causes deterioration of product quality such as the formation of organochlorine components upon ethylene oligomerization.

Such being the case, the process for producing an ethylenic oligomer by using a Ziegler based catalyst involves a fear of deteriorating the catalytic activity due to water present in the reaction system, particularly the water introduced from a reaction solvent into the reaction system. In particular, in the case of recovering unreacted ethylene from the oligomerization product, deactivating the catalyst and deashing, thereafter recycling the organic solvent separated by distillation through the reaction system and reusing it as a reaction solvent, there has been a fear of a large amount of water being mixed in the reaction system during the operation. Accordingly, it has been desired to decrease the amount of water mixed in the reaction system, particularly the amount of water in the reaction solvent to be recycled and at the same time, to maintain the catalytic activity at a highest possible level.

In the method comprising the above-mentioned process, in the case of recycling the organic solvent finally obtained in a fractionating system through the oligomerization reaction system for the purpose of reuse, considerable amounts of resultant olefins as ethylenic oligomers are mixed in the organic solvent. In general, the ethylenic oligomer produced by the foreging process contains impurities such as paraffin, internal olefin and branched olefin, which impurities cause marked deterioration in the quality of a polyethylene resin and the like as the final products. In particular, it has been proved that in the case of recycling an organic solvent in the oligomerization reaction system for use as a reaction solvent, the foregoing unfavorable result is made remarkable by the existence of an olefin which is other than ethylene and is contained in the organic solvent. Moreover the catalyst, which is formulated in the presence of a solvent, brings about the possibility of causing deterioration in catalytic activity or clogging in a catalyst feed line due to olefin polymerization.

DISCLOSURE OF THE INVENTION

That is to say, the present invention consists in providing a method for maintaining a catalytic activity at a high level in a process for producing an ethylenic oligomer which employs a Ziegler based catalyst and recyclingly uses a reaction solvent.

Moreover, the present invention consists in providing a method capable of affording a highly pure ethylenic oligomer free from an impurity in a process for producing an ethylenic oligomer which employs a Ziegler based catalyst and recyclingly uses a reaction solvent.

In view of the above-mentioned subject, intensive extensive research and investigation were accumulated by the present inventors. As a result, it has been found that the objects of the present invention can be achieved by reducing water present in the reaction system, particularly the water introduced from a reaction solvent into the reaction system, especially from an organic reaction solvent to be recyclingly used thereinto. Further it has been found that the objects of the present invention can be achieved by reducing olefinic components that are other than ethylene and are present in the reaction system, particularly the aforesaid olefinic components introduced from a reaction solvent into the reaction system, especially from an organic reaction solvent to be recyclingly used thereinto. Thus the present invention has been accomplished on the basis of the foregoing findings and information.

Specifically, the present invention provides a process for producing an ethylenic oligomer which comprises subjecting ethylene to oligomerization reaction in an organic solvent in the presence of a Ziegler based catalyst, and recyclingly using for the oligomerization reaction, the organic solvent separated by distillng the resultant oligomerization reaction product, wherein the water concentration in the oligomerization reaction system is at most 8 ppm by weight, in particular the water concentration in the organic solvent to be recycled in the oligomerization reaction system is at most 8 ppm by weight (first aspect of the present application).

In addition, the present invention provides a process for producing an ethylenic oligomer which comprises subjecting ethylene to oligomerization reaction in an organic solvent in the presence of a Ziegler based catalyst, and recyclingly using for the oligomerization reaction, the organic solvent separated by distillng the resultant oligomerization reaction product, wherein the concentration of olefins having at least three carbon atoms in the organic solvent to be recycled in the oligomerization reaction system is at most 2% by weight (second aspect of the present application).

THE MOST PREFERRED EMBODIMENT TO CARRY OUT THE INVENTION

Figure 1:
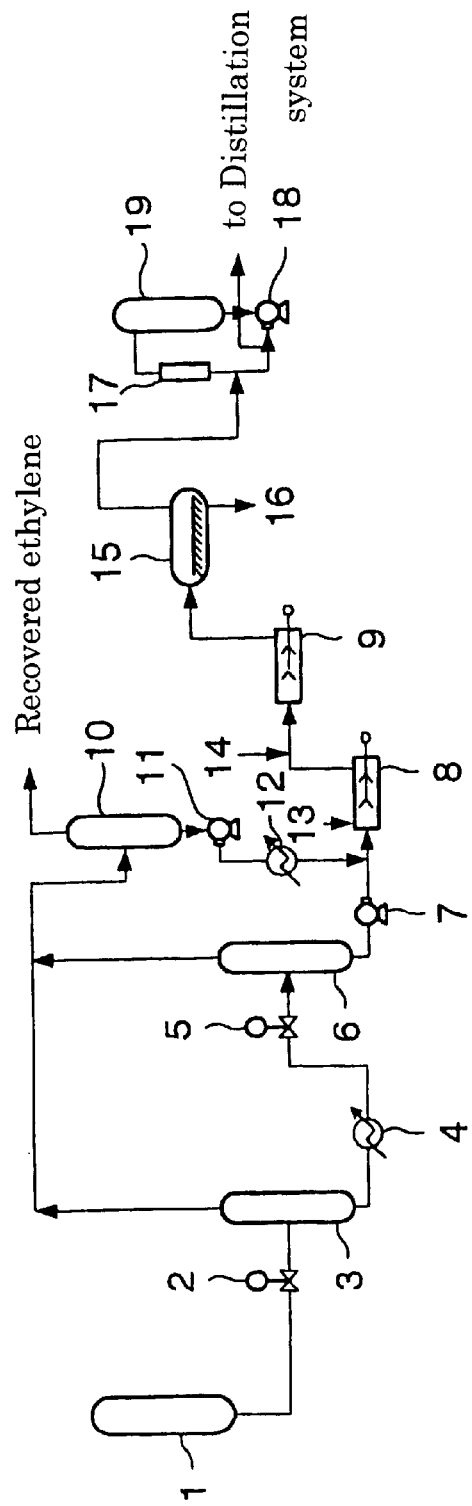
FIG. 1 and FIG. 2 are each a schematic process flow diagram which shows the production process for carrying out the present invention.

In the following, more detailed description will be given of the present invention. In the present invention, the ethylenic oligomer is obtained by oligomerizing ethylene in the presence of a Ziegler based catalyst, which consists of the combination of (A) a transition metal compound, (B) an organoaluminum and (C) a tertiary component to be used as desired. There is used as the transition metal compound (A), the compound represented by the general formula:

$$MX_xY_yO_z \quad (I)$$

wherein M is a zirconium atom or a titanium atom, X is a halogen atom (chlorine atom, bromine atom or iodine atom), Y is RO—, $R_2N$—, —OCOR, —$OSO_3R$, R—, —Cp (cyclopentadienyl), wherein R is a straight chain or branched chain alkyl group having 1 to 20 carbon atoms or β diketonato represented by the general formula (II):

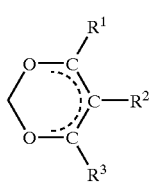

(II)

wherein $R^1$, $R^2$ and $R^3$ are each independently a hydrogen atom, an alkyl group having 1 to 20 carbon atoms or an alkyl group which is substituted with a halogen atom and which has 1 to 20 carbon atoms with the proviso that one of $R^1$, $R^2$ and $R^3$ is an alkyl group which is substituted with a halogen atom and which has 1 to 20 carbon atoms, x, y and z are each an integer from 0 to 4 with the proviso that x+y+z=4.

The above-mentioned compound is specifically exemplified by $ZrCl_4$, $ZrBr_4$, $ZrI_4$, $ZrBrCl_3$, $ZrBr_2Cl_2$ $TiCl_4$, $TiBr_4$, $TiI_4$, $TiBrCl_3$, $TiBr_2C_2$, $Zr(OC_2H_5)_4$, $Zr(OC_2H_5)_2Cl_2$, $Zr(O-n-C_3H_7)_4$, $Zr(O-n-C_3H_7)_2Cl_2$, $Zr(O-iso-C_3H_7)_4$, $Zr(O-iso-C_3H_7)_2Cl_2$, $Zr(O-n-C_4H_9)_4$, $Zr(O-n-C_4H_9)_2Cl_2$, $Zr(O-iso-C_4H_9)_4$, $Zr(O-iso-C_4H_9)_2Cl_2$, $Zr(O-tert-C_4H_9)_4$, $Zr(O-tert-C_4H_9)_2$ $Cl_2$, $Zr((CH_3)_2N)_4$, $Zr((C_2H_5)_2N)_4$, $Zr((n-C_3H_7)_2N)_4$, $Zr((iso-C_3H_7)_2 N)_4$, $Zr((n-C_4H_9)_2 N)_4$, $Zr((tert-C_4H_9)_2 N)_4$, $Zr(OSO_3 CH_3)_4$, $Zr(OSO_3C_2H_5)_4$, $Zr(OSO_3 C_3H_7)_4$, $Zr(OSO_3C_4H_9)_4$, $ZrCp_2Cl_2$, $ZrCp_2$ ClBr, $Ti(OC_2H_5)_4$, $Ti(OC_2H_5)_2$ $Cl_2$, $Ti(O-n-C_3H_7)_4$, $Ti(O-n-C_3H_7)_2Cl_2$, $Ti(O-iso-C_3H_7)_4$, $Ti(O-iso-C_3H_7)_2$ $Cl_2$, $Ti(O-n-C_4H_9)_4$, $Ti(O-n-C_4H_9)_2$ $Cl_2$, $Ti(O-iso-C_4H_9)_4$, $Ti(O-iso-C_4H_9)_2$ $Cl_2$, $Ti(O-tert-C_4H_9)_4$, $Ti(O-tert-C_4H_9)_2Cl_2$, $Ti((CH_3)_2N)_4$, $Ti((C_2H_5)_2N)_4$, $Ti((n-C_3H_7)_2N)_4$, $Ti((iso-C_3H_7)_2N)_4$, $Zr(n-C_4H_9)_2N)_4$, $Ti((tert-C_4H_9)_2N)_4$, $Ti(OSO_3CH_3)_4$, $Ti(OSO_3C_2H_5)_4$, $Ti(OSO_3C_3H_7)_4$, $Ti(OSO_3C_4H_9)_4$, $TiCp_2Cl_2$, $TiCp_2ClBr$, $Zr(OCOC_2H_5)_4$, $Zr(OCOC_2H_5)_2Cl_2$, $Zr(OCOC_3H_7)_4$, $Zr(OCOC_3H_7)_2Cl_2$, $Zr(OCOC_3H_7)_4$, $Zr(OCOC_3H_7)_2Cl_2$, $Zr(OCOC_4H_9)_4$, $Zr(OCOC_4H_9)_2$ $Cl_2$, $Ti(OCOC_2H_5)_4$, $Ti(OCOC_2H_5)_2$ $Cl_2$, $Ti(OCOC_3H_7)_4$, $Ti(OCOC_3H_7)_2$ $Cl_2$, $Ti(OCOC_3H_7)_4$, $Ti(OCOC_3H_7)_2Cl_2$, $Ti(OCOC_4H_9)_4$, $Ti(OCOC_4H_9)_2Cl_2$, $ZrCl_2(HCOCFCOF)_2$ and $ZrCl_2(CH_3COCFCOCH_3)_2$.

The organoaluminum (B) is exemplified by the compound represented by the general formula:

$$AlY_aX_bO_cN_d \quad (III)$$

wherein X is a halogen atom (chlorine atom, bromine atom or iodine atom), Y is RO—, $R_2$ N—, —OCOR, or R—, wherein R is a straight chain or branched chain alkyl group having 1 to 20 carbon atoms, and a, b, c and d are each an integer from 0 to 3 with the proviso that a +b+c+d_3, and/or by the compound represented by the general formula:

$$Al_2Y_{a'}X_{b'}O_{c'}N_{d'} \quad (IV)$$

wherein X is a halogen atom (chlorine atom, bromine atom or iodine atom), Y is RO—, $R_2$ N—, —OCOR, —RCOCR', COR" or R—, wherein R, R' and R" are each a straight chain or branched chain alkyl group having 1 to 20 carbon atoms, and a', b', c' and d' are each an integer from 0 to 6 with the proviso that a'+b'+c'+d'=6.

Examples of the compound represented by the general formula (III) include $Al(CH_3)_3$, $Al(C_2H_5)_3$, $Al(C_3H_7)_3$, $Al(iso-C_3H_7)_3$, $Al(C_4H_9)_3$, $Al(iso-C_4H_9)_3$, $Al(C_5H_{11})_3$, $Al(C_6H_{13})_3$, $Al(C_8H_{17})_3$, $Al(C_2H_5)_2Cl$, $Al(C_2H_5)_2Br$, $Al(C_2H_5)_2I$, $Al(C_2H_5)Cl_2$, $Al(C_2H_5)Br_2$, $Al(C_2H_5)_2$, $AlC_2H_5(OC_2H_5)2$, $AlC_2H_5(OC_3H_7)_2$, $AlC_2H_5(OC_4H_9)_2$, $Al(OC_2H_5)_2Cl$, $Al(OC_3H_7)_2Cl$, $Al(OC_4H_9)_2Cl$, $Al(OC_2H_5)Cl_2$, $Al(OC_3H_7)Cl_2$, $AlOC_4H_9)Cl_2$, $AlC_2H_5(OCOC_2H_5)_2$ $AlC_2H_5(OCOC_3H_7)_2$, $AlC_2H_5$ $(OCOC_4H_9)_2$, $Al(OCOC_2H_5)_2$ Cl, $Al(OCOC_3H_7)_2Cl$, $Al(OCOC_4H_9)_2Cl$, $Al(OCOC_2H_5)Cl_2$, $Al(OCOC_3H_7)Cl_2$, $Al(OCOC_4H_9)Cl_2$, $Al(C_2H_5)_2OC_2H_5$, $Al(C_2H_5)_2OC_3H_7$, $Al(C_2H_5)_2OC_4H_9$, $Al(C_2H_5)_2N(C_2H_5)_2$, $Al(C_2H_5)_2N(C_3H_7)_2$ and $Al(C_2H_5)_2N(C_4Hl)_2$. Examples of the compound represented by the general formula (IV) include $Al_2(CH_3)_3Cl_3$, $Al_2(CH_3)_3Br_3$, $Al_2(C_2H_5)_3Cl_3$, $Al_2(C_2H_5)_3Br_3$, $Al_2(C_2H_5)_3$, $Al_2(C_2H_5)_2BrCl_2$, $Al_2(C_3H_7)_3Cl_3$, $Al_2(iso-C_3H_7)_3Cl_3$, $(C_4H_9)_3C_3$, $Al_2(iso-C_4H_9)_3$ $Cl_3$, $Al_2(C_5H_{11})_3Cl_3$, $Al_2$ $(C_8H_{17})_3$ $Cl_3$, $Al_2(C_2H_5)_2(CH_3)Cl_3$, $Al_2(OC_2H_5)_3Cl_3$, $Al_2(OC_3H_7)_3$ $Cl_3$, $Al_2(OC_4H_9)_3Cl_3$, $Al_2(OCOC_2H_5)_3Cl_3$, $Al_2(OCOC_3H_7)_3Cl_3$ and $Al_2(OCOC_4H_9)_3$ $Cl_3$.

As the tertiary component (C) which is used as desired, there is usable at least one compound selected from sulfur compounds, phosphorus compounds and nitrogen compounds. The tertiary component contributes to enhancing the purity of an ethylenic oligomer as the objective product.

The sulfur compound needs only to be an organosulfur compound without specific limitation, and is preferably exemplified by dimethyl sulfide, diethyl sulfide, dipropyl sulfide, dihexyl sulfide, dicyclohexyl sulfide, thioethers such as diphenyl thioether: dialkyl disulfide compounds such as dimethyl disulfide, diethyl disulfide, dipropyl disulfide, dibutyl disulfide, dihexyl disulfide, dicyclohexyl disulfide and ethylmethyl disulfide: thiophenes such as thiophene, 2-methyl-thiophene, 3-methylthiophene, 2,3-dimethylthiophene, 2-ethylthiophene and benzothiophene and heterocyclic sulfur compounds such as tetrahydrothiophene and thiopyrane: aromatic sulfur compounds such as diphenyl sulfide, diphenyl disulfide, methylphenyl disulfide, methylphenyl sulfide: thiourea: and sulfides such as methyl sulfide, ethyl sulfide and butyl sulfide.

The phosphorus compound needs only to be an organophosphorus compound without specific limitation, and is preferably exemplified by phosphines such as triphenylphosphine, triethylphosphine, tributylphosphine, tripropylphosphine, trioctylphosphine and tricyclohexylphosphine.

The nitrogen compound needs only to be an organonitrogen compound without specific limitation, and is preferably exemplified by organoamines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine and picoline.

There are preferably usable in the present invention, the sulfur compounds, phosphorus compounds and nitrogen compounds each as mentioned above, of which is particularly preferably usable one or two or more compounds selected from dimethyl disulfide, thiophenes, thiourea, triphenylphosphine, tributyl phosphine, trioctylphosphine and aniline.

The oligomerization reaction of ethylene according to the present invention is put into practice usually in an organic solvent. Examples of the organic solvent include alicyclic compounds such as cyclohexane and decalin, aromatic hydrocarbons such as benzene, toluene, xylene, chlorobenzene, ethylbenzene, dichlorobenzene and chlorotoluene, halogenide thereof, aliphatic hydrocarbons such as pentane, hexane, heptane, octane, nonane and decane, halogenated aliphatic hydrocarbons such as dichloroethane and dichlorobutane, and the like solvents.

With regard to the blending proportions of the foregoing components (A), (B) and (C) and the foregoing organic solvent in the present invention, the amount of the component (A) is usually 0.01 to 5 mmol, preferably 0.03 to 1 mmol, the amount of the component (B) is usually 0.05 to 15 mmol, preferably 0.06 to 3 mmol, and the amount of the component (C) is usually 0.05 to 20 mmol, preferably 0.1 to 10 mmol in the case of using the above-mentioned sulfur compound, preferably 0.05 to 5 mmol in the case of using the aforesaid nitrogen or phosphorus compound, on the basis of 250 ml of the organic solvent.

In addition, more preferable result is obtainable by setting the blending proportions of the foregoing components (A) and (B) to 1 to 15 expressed in terms of Al/Zr (molar ratio).

The oligomerization reaction in the present invention is carried out usually at a temperatue in the range of 100 to 150° C. under pressure of 30 to 90 kg/cm$^2$·G (2.94 to 8.82 MPa). The reaction time, which varies depending upon the temperature and pressure and accordingly can not be unequivocally determined, is usually 10 to 60 minutes, approximately.

The ethylenic oligomers to be obtained by using ethylene as the starting material in the process according to the present invention are a variety of oligomers each having the number of carbon atoms of 4 or more, preferably 4 to 24, particularly 4 to 18. Specific examples thereof include 1-butene, 1-hexene, 1-octene, 1-decene, 1-dodecene, 1-tetradecene, 1-hexadecene and 1-octadecene. The ethylenic oligomers are obtained as mixed products of these oligomers.

In the process according to the present invention, the liquid reaction product obtained by the oligomerization reaction of ethylene is subjected to subsequent recovery of unreacted ethylene, deactivation of the catalyst and deashing treatment. In this case, it is necessary to maintain the temperature of the liquid reaction product after the completion of the oligomerization reaction at 90° C. or higher. The foregoing temperature is not specifically limited provided that it is 90° C. or higher, but is in the range of usually 90 to 150° C., preferably 100 to 130° C. The foregoing temperature, when being unreasonably high, is unfavorable, since it sometimes brings about deterioration of product purity.

The amount of by-produced polymer, which varies depending upon the reaction conditions, is not unequivocal, but is usually 300 to 500 ppm. The by-produced polymer is dissolved in the liquid reaction product when the temperature thereof is kept at 90° C. or higher, thereby enabling to proceed with stable running irrespective of the type of the organic solvent to be used for the polymerization reaction.

Subsequently the catalyst is subjected to deactivation treatment by introducing a deactivating agent at a pressure of the treatment system of 4 kg/cm$^2$·G(0.39 MPa), approximately. Examples of the deactivating agent to be used therein include basic nitrogen compounds, water, alcohols, carboxylic acids and phenols. The basic nitrogen compounds among them are exemplified by ammonia and amines such as methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine and picoline.

In the present invention, the above-mentioned deactivation treatment is followed by deashing treatment and further recovery of the organic solvent and unreacted ethylene by distillation. The recovered organic solvent and unreacted ethylene are each recycled through the oligomerization reaction system.

The objective ethylenic oligomers are obtained as desirable mixed products of various ethylenic oligomers by means of multistage distillation. The mixed products can be obtained in large amounts as ethylenic oligomers each having desirable number of carbon atoms by properly selecting the reactioin conditions.

The organic solvent which has been separated and recovered in the above-mentioned distillation step is recycled through the oligomerization reaction system for use as the reaction solvent. In this case, it is necessary in the first aspect of the present application to set the water concentration in the solvent on at most 8 ppm by weight. The water concentration exceeding 8 ppm by weight results in deterioration in a catalytic activity, thus making it impossible to maintain a high activity. Accordingly it is preferable in the present invention to further decrease the water concentration in the organic solvent to be recycled to at most 5 ppm by weight.

As a method for decreasing the water concentration in the organic solvent to be recycled, a general procedure such as distillation and adsorption can be used.

In the case where the organic solvent which has been separated and recovered in the above-mentioned distillation step is recycled through the oligomerization reaction system for use as the reaction solvent, it is necessary in the second aspect of the present application to set the concentration of the olefin having 3 or more carbon atoms, for instance, the olefin having 4 or 8 carbon atoms in the solvent on at most 2% by weight. The aforesaid concentration exceeding 2% by weight brings about an increase in impurities in the resultant ethylenic oligomers, thus deteriorating the quality of polyethylene resin and the like as the final product. For this reason, the concentration of the olefin in the organic solvent to be recycled is set on preferably at most 1% by weight, more preferably at most 0.5% by weight.

It is preferable in the present invention to combine the first and second aspects thereof, viz., to set the concentration of the olefin having 3 or more carbon atoms, for instance, the olefin having 4 or 8 carbon atoms in the solvent to be recycled through the oligomerization reaction system on at most 2% by weight in the first aspect thereof, and also to set the water concentration in the solvent to be recycled through the oligomerization reaction system on at most 8 ppm by weight in the second aspect thereof.

In order to decrease the water concentration in the solvent which has been separated and recovered within the prescribed range according to the present invention and at the same time, to decrease the concentration of olefin having 3 or more carbon atoms in the solvent which has been separated and recovered within the prescribed range according thereto, the following distillation procedure is preferably carried out.

Distillation equipment preferably comprises a plurality of distillation columns. In the case of separating and recovering the solvent with two distillation columns, it is possible as the process flow diagram of distillation equipment to separate water and ethylenic oligomer lighter than the solvent at the overhead of a first distillation column, introduce the bottom into a second distillation column, and recover the solvent at the overhead of the second distillation column. It is preferable in this case to set the theoretical number of plates to at least 30, and the reflux ratio to at least 4 in each of the distillation columns.

In the following, some description will be given of the preferred embodiments of the present invention with reference to the attached drawings. FIG. 1 is a schematic process flow diagram which shows the production process for carrying out the present invention. The liquid reaction product which is produced in a reactor 1 and is composed of a Ziegler based catalyst, an organic solvent, unreacted ethylene and ethylenic oligomers is supplied to a first stage flash tank 3 via a control valve 2, and further to a second stage flash tank 6 via a control valve 5. The liquid product after the first stage flashing, prior to supply to the second stage flash tank, is heated in a heat exchanger 4 to be kept at a prescribed temperature or higher. In these flash tanks the unreacted ethylene which is dissolved in the liquid reaction product is recovered. Then the liquid reaction product is sent to a deactivator 8, where the catalyst is deactivated with a deactivating agent 13. Slight amount of light ethylenic oligomer accompanying the recovered ethylene is recovered in a pot 10, and is sent to the deactivator 8, and then to a deasher 9, and after cleaning with cleaning water 14, to a separating tank 15. Therein the deactivated liquid is separated into oil phase and water phase, and the water phase is discarded outside the system as waste water 16. The oil phase is sent to a dissolving tank 19 equipped with a heat exchanger 17 and a pump 18, is heated to again dissolve the polymer therein completely, and thereafter is sent to the distillation system, where the solvent and the ethylenic oligomer are fractionated.

Figure 3:
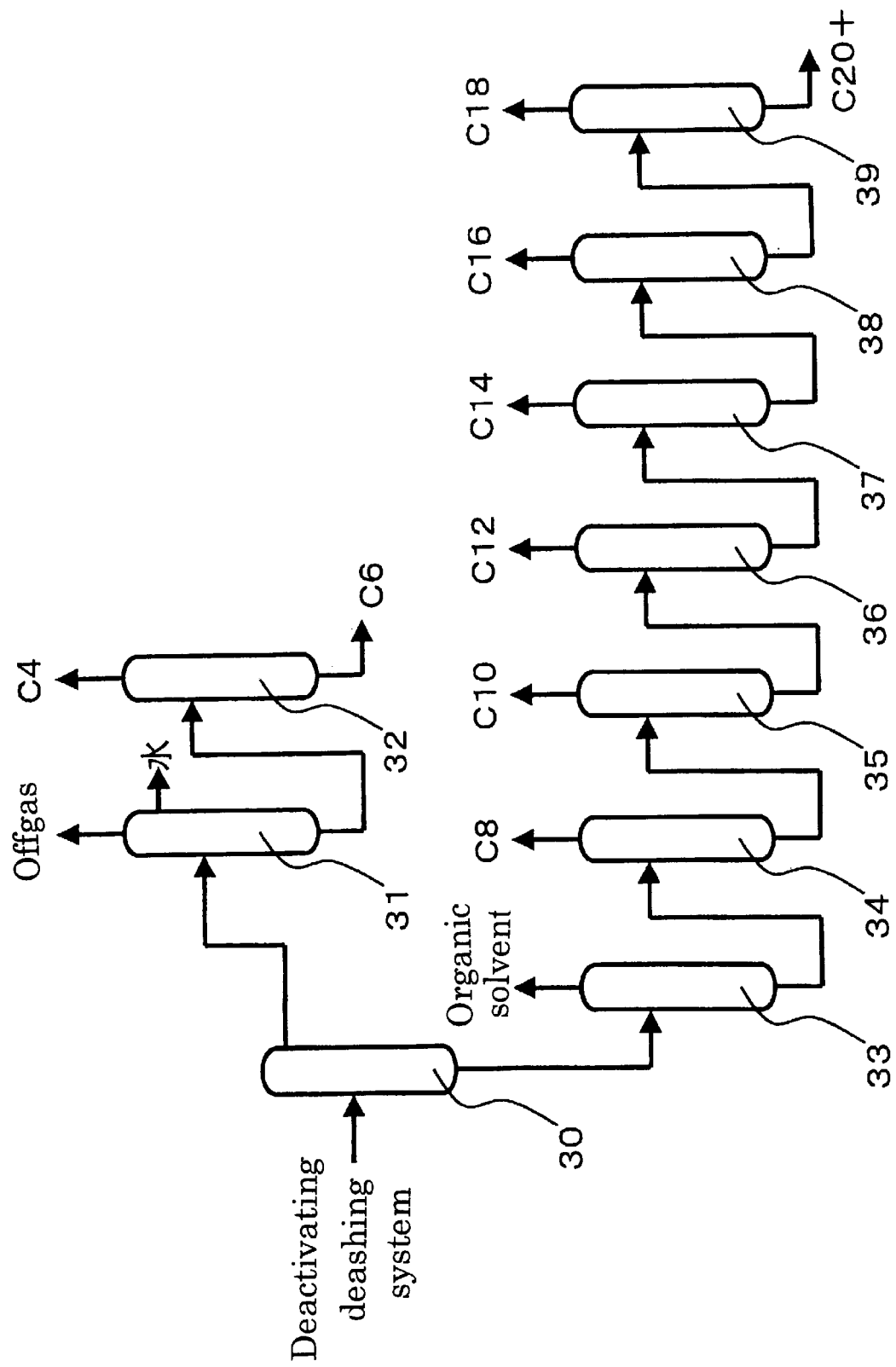
FIG. 3 and FIG. 4 are each a schematic process flow diagram which shows an example of carrying out distillation in the process of the present invention.
Figure 4:
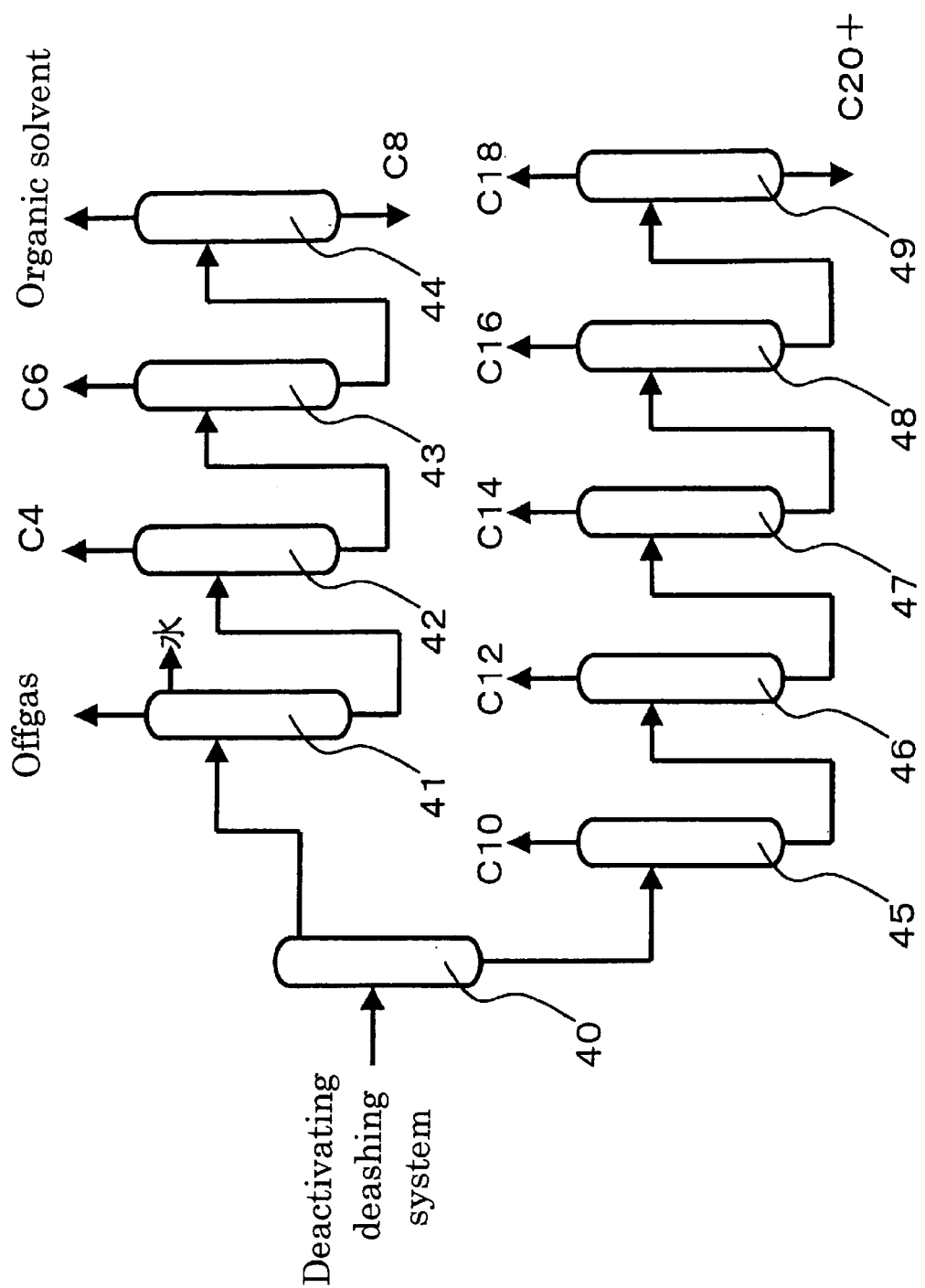

Mention can be made of various distillation flow diagrams, for instance, two flow diagrams as illustrated on FIGS. 3 and 4.

Example of Distillation Flow Diagram 1 (FIG. 3)

The liquid after the deashing treatment is sent to a first distillation column 30, where the liquid composed principally of ethylenic oligomer with C-6 and less is withdrawn at the top, whereas the liquid composed principally of ethylenic oligomer with C-8 and more and the organic solvent is withdrawn at the bottom.

The overhead liquid in the first distillation column 30 is introduced in the second distillation column 31, where offgas and water are withdrawn at the top, and the ethylenic oligomer with C-4 and more obtained at the bottom is introduced in a third distillation column 32, where the ethylenic oligomer with C-4 is obtained at the top, and the ethylenic oligomer with C-6 is obtained at the bottom.

The bottom in the first distillation column 30 is introduced in a fourth distillation column 33, where the organic solvent is obtained at the top, and the liquid composed principally of ethylenic oligomer with C-8 or more is obtained at the bottom. In the present invention, the organic solvent obtained therein is again recycled through the oligomerization reaction system as the reaction solvent. The bottom in the fourth distillation tower 33 is consecutively introducced in the same manner as the foregoing, into distillation columns 34, 35, 36, 37, 38 and 39, where ethylenic oligomers with C-8, C-10, C-12, C-14, C-16 and C-18, respectively are obtained at the top, and the liquid composed principally of ethylenic oligomer with C-20 or more is obtained at the bottom of the final distillation tower 39.

Example of Distillation Flow Diagram 2 (FIG. 4)

The liquid after the deashing treatment is sent to a first distillation column 40, where the liquid composed principally of ethylenic oligomer with C-8 and less and the organic solvent is withdrawn at the top, whereas the liquid composed principally of ethylenic oligomer with C-10 and more is withdrawn at the bottom. The overhead liquid in the first distillation column 40 is introduced in the second distillation column 41, where offgas and water are withdrawn at the top, and the ethylenic oligomer with C-4 and more and the organic solvent that are obtained at the bottom are consecutively introducced in a third distillation column 42, a fouth distillation column 43 and a fifth distillation column 44, where the ethylenic oligomer with C-6 and the organic solvent are obtained at the top, and ethylenic oligomer with C-8 is obtained as the bottom 44. In the present invention, the organic solvent obtained therein is again recycled through the oligomerization reaction system as the reaction solvent. The bottom in the distillation column 40 is consecutively introducced in the same manner as the foregoing, into distillation columns 45, 46, 47, 48 and 49, where ethylenic oligomers with C-10, C-12, C-14, C-16 and C-18, respectively are obtained at the top, and the liquid composed principally of ethylenic oligomer with C-20 and more is obtained at the bottom of the final distillation tower 49.

By virtue of the process for producing an ethylenic oligomer according to the present invention wherein a Ziegler based catalyst is employed and a reaction solvent is recyclingly used, it is made possible to maintain the catalytic activity of the foregoing catalyst by decreasing the water concentration in an organic solvent to be recycled through the oligomerization reaction system to a prescribed level or lower. It is also made possible to obtain a highly pure ethylenic oligomer free from an impurity by setting the concentration of olefin having 3 and more carbon atoms in the reaction solvent to be recycled through the above-mentioned oligomerization reaction system on at most 2% by weight.

In the following, the present invention will be described in more detail with reference to working examples, which however shall never limit the present invention thereto.

EXAMPLE 1

[Preparation of Catalyst]

In a 500 milliliter (mL) flask equipped with a stirrer were introduced in an atmosphere of argon, 25 mmol of zirconium tetrachloride anhydride ($ZrCl_4$) and 250 mL of dry cyclohexane with stirring for 10 minutes at room temperature. To the mixture thus prepared were added triethylaluminum [$(C_2H_5)_3Al$] and then ethylaluminum sesquichloride [$(C_2H_5)_3Al_2Cl_3$] wherein the amounts of the triethylaluminum and ethylaluminum sesquichloride were regulated to $(C_2H_5)_3Al_2Cl_3/(C_2H_5)_3Al$ being 3.5 (molar ratio) and [$(C_2H_5)_3Al_2 Cl_3+(C_2H_5)_3Al]/ZrCl_4$ being 7 (molar ratio). After adding all the components, the resultant mixture was heated at 70° C. for 2 hours in an atmosphere of argon under stirring to form a complex so that liquid catalyst was prepared.

[Oligomerization Reaction]

Oligomerization reaction was continuously carried out by the use of a complete mixing tank type reactor (internal volume of one liter). The above-prepared liquid catalyst was mixed with cyclohexane which had been dried in an atmosphere of argon so that the concentration of the zirconium tetrachloride was adjusted to 0.08 mmol/1 of cyclohexane. Further, thiophene was added to the mixture in an amount of three times molar ratio to the zirconium tetrachloride to prepare a catalytic solution. Subsequently a definite amount of the catalytic solution was fed in the reactor (700 cc/hour). The oligomerization reaction was carried out at 120° C. at 65 kg/cm²·G (6.4 MPa) under stirring at 500 rpm at a liquid level equivalent to 500 cc for retention time of 43 minutes, during which time highly pure ethylene gas was continuously fed in the reactor so as to maintain the reaction pressure at 65 kg/cm²·G.

The reaction conditions and the results are given in Table 1.

TABLE 1

| | |
|---|---|
| ZrCl$_4$ (mmol/hour) | 0.08 |
| Ethylaluminum sesquichloride (mmol/hour) | 0.436 |
| Triethylaluminum (mmol/hour) | 0.124 |
| Cyclohexane (cc/hour) | 700 |
| Reaction temperature (° C.) | 120 |
| Reaction pressure (kg/cm² · G) | 65 |
| Reaction time (minute) | 43 |
| Catalytic activity (kg/g · ZrCl$_4$) | 12.6 |
| Ethylenic oligomer | |
| C-4 (% by wt) | 14.9 |
| C-6 (% by wt) | 15.4 |
| C-8 (% by wt) | 14.1 |
| C-10~18 (% by wt) | 41.3 |
| C- ≥ 20 (% by wt) | 14.3 |
| C-18 purity | 94.5 |

[Deactivation Treatment of Catalyst]

Figure 2:
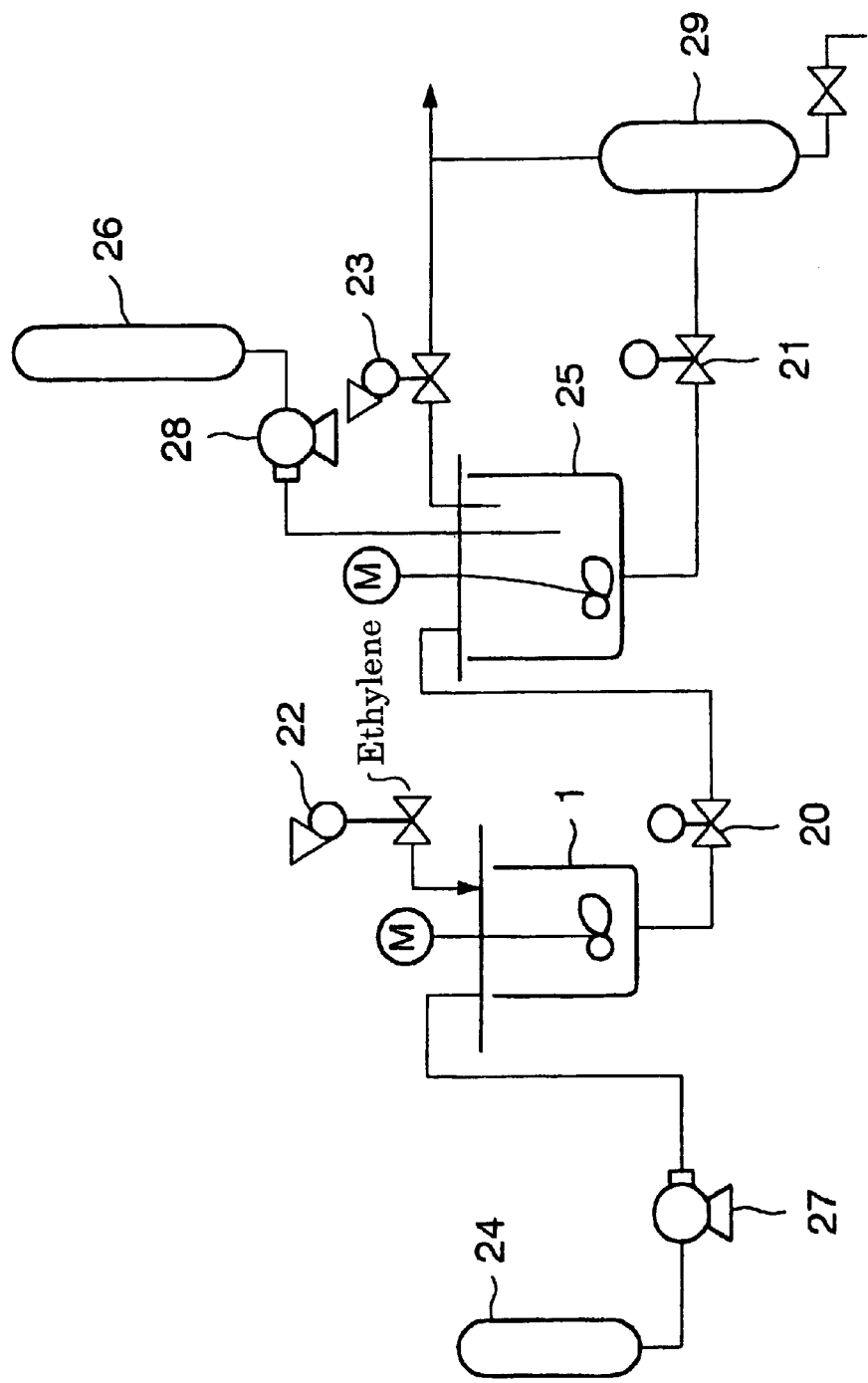

The deactivation treatment of catalyst was carried out by continuously supplying the deactivating tank with the liquid reaction product which had been obtained in the foregoing oligomerization reaction at a flow rate of cyclohexane of 546 g/hour (700 cc/hour) at a flow rate of ethylenic oligomer of 225 g/hour, making a total of 771 g/hour. A deactivating agent consisting of 10% by weight of aqueous ammonia was supplied at 28 g/hour. The deactivating tank was operated at 100° C. at 4 kg/cm²·G (0.39 MPa) under stirring at 700 rpm by the use of the equipment as illustrated in FIG. 2, wherein the symbols 24, 25 and 26 are pot, deactivating tank and aqueous ammonia tank, respectively. The liquid product after the deactivation treatment was filtered to filter off wax component by using filter paper. The resultant filtrate was washed twice with deionized water in an amount two times that of the filtrate, and subsequently dried with potassium carbonate anhydride. The colorless transparent liquid reaction product thus obtained was analysed by gas chromatography to determine the distribution and purity of the ethylenic oligomer as the objective product. The product distribution was found by calculation through Schultz·Flory distribution from the result of gas chromatography for C-10 and more based on the operational loss.

[Distillation Operation]

The resultant oligomerization reaction liquid which had been subjected to deactivation treatment was separated by means of distillation to recover cyclohexane by the following manner.

The resultant oligomerization reaction liquid was introduced in an Oldshue distillation equipment (first distillation column) having an inside diameter of 40 mm at a flow rate of 360 g/hour. The first distillation column had the number of theoretical plates of 15 in the enriching section and 15 in the stripping section, and was operated at atmospheric pressure at a temperature of 66.1° C. at the overhead and at a temperature of 90.7° C. at the bottom at a reflux ratio of 5. The liquid composed principally of ethylenic oligomer with C-6 and less and cyclohexane was withdrawn at the overhead at a flow rate of 47 g/hour, and the liquid composed principally of most of cyclohexane and ethylenic oligomer with C-8 and more was withdrawn at the bottom at a flow rate of 313 g/hour.

Figure 5:
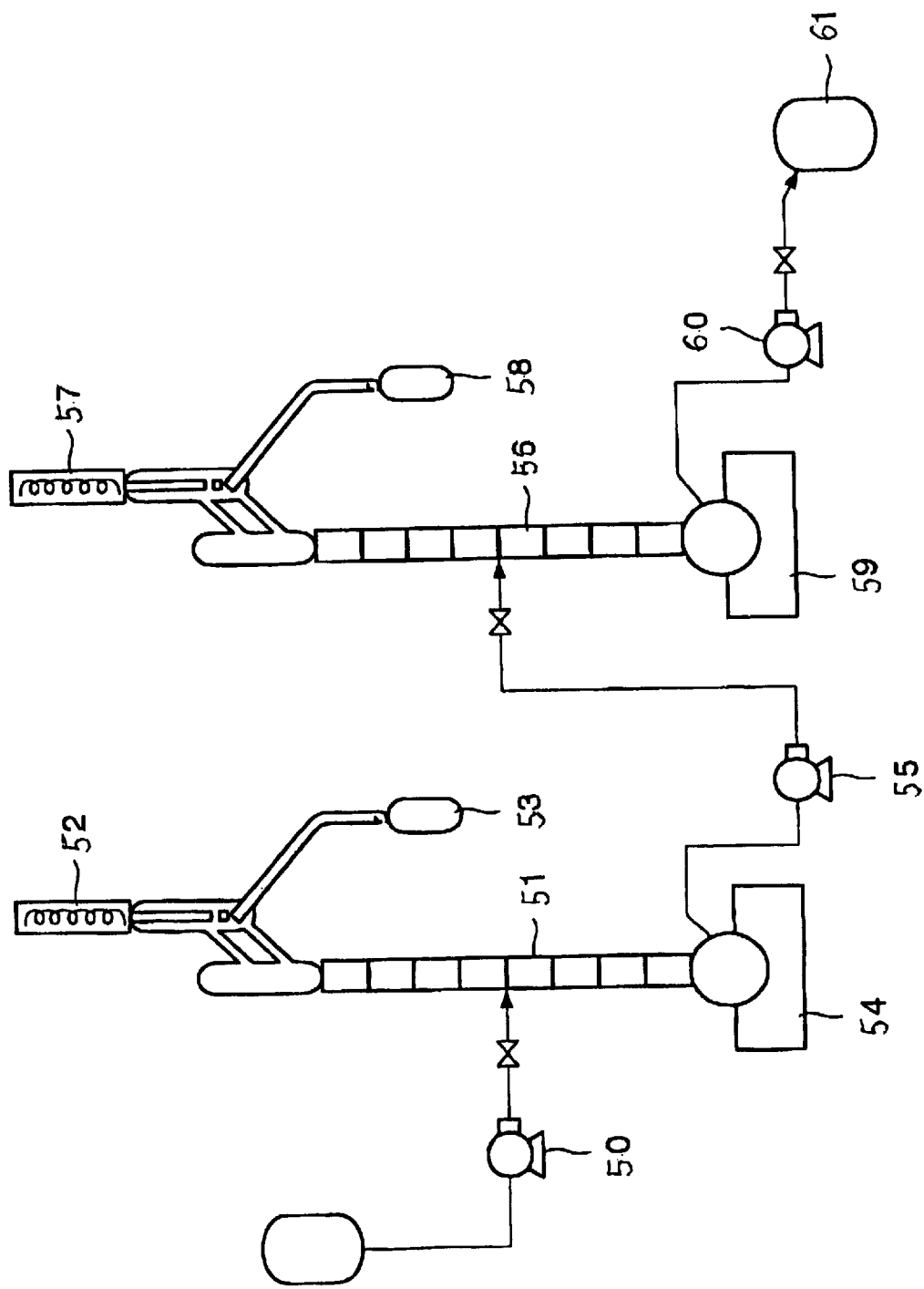
FIG. 5 is a schematic process flow diagram which shows the production process for carrying out distillation in the working examples of the present invention

The bottom from the first distillation column was introduced in another Oldshue distillation equipment (second distillation column) having an inside diameter of 40 mm. The second distillation column had the number of theoretical plates of 15 in the enriching section and 15 in the stripping section, and was operated at atmospheric pressure at a temperature of 80.0° C. in the overhead and at a temperature of 170.9° C. in the bottom at a reflux ratio of 5. The liquid composed principally of cyclohexane was withdrawn at the overhead at a flow rate of 170 g/hour, and the liquid composed principally of cyclohexane and ethylenic oligomers with C-8 and more was withdrawn at the bottom at a flow rate of 143 g/hour. The overhead obtained from the second distillation column had a water concentration being 8 ppm by wieght and a concentration of olefin with C-3 and more being 0.35% by weight. The above-mentioned distillation operation was carried out by using the equipment as illustrated in FIG. 5, wherein the symbols denote the followings.

51: first distillation column, 52 and 57: condenser, 53 and 58: receiver, 54 and 59: oil bath, 56: second distillation column, 61: pot.

Subsequently, the overhead which had been obtained from the second distillation column in the above-mentioned manner, and which was composed principally of cyclohexane was treated with a molecular sieve to reduce the water concentration to at most one ppm by weight, and was utilized for the preparation of catalyst and for oligomerization reaction.

[Preparation of Catalyst]

In a one liter (L) flask equipped with a stirrer were introduced in an atmosphere of argon, 100 mL of zirconium tetrachloride anhydride (ZrCl$^4$) and the foregoing liquid composed principally of cyclohexane having a water concentration of at most one ppm by weight with stirring for 10 minutes. To the mixture thus prepared were added 158.3 mmol of triethylaluminum (TEA) with stirring for 10 minutes and then 541.7 mmol of ethylaluminum sesquichloride (EASC) followed by stirring at 70° C. for 2 hours to form a complex.

Subsequently, in a 500 mL three-neck flask were introduced 250 ml of the foregoing liquid composed principally of cyclohexane having a water concentration of at most one ppm by weight and the above-prepared solution of the complex so that the solution contained 0.12 mmol of ZrCl$_4$, 0.65 mmol of EASC and 0.19 mmol of TEA. To the resultant mixture was added 0.36 mmol of thiophene with stirring for 10 minutes, so that liquid catalyst was prepared.

[Preparation Example of Ethylenic Oligomer (Oligomerization of Ethylene)]

In a one liter (L) autoclave equipped with a stirrer was introduced by pressurizing in an atmosphere of dry argon, the liquid catalyst which had been prepared in the above-mentioned "Preparation of catalyst", while the autoclave was maintained at 50 to 60° C. After completing the supply of the liquid catalyst, stirring was started, highly pure ethylene gas was promptly blown into the autoclave until the pressure therein reached 65 kg/cm²·G, and thereafter the temperature was raised to 120° C. The blowing in of the ethylene was continued in an amount necessary for maintaining the foregoing pressure, while the reaction was continued for 30 minutes under the above-mentioned reaction conditions. After the completion of the reaction, the autoclave was cooled, depressurized, and was incorporated with 10 mL of water as the deactivating agent to deactivate the catalyst. As a result, the catalytic activity was made to be the figures as given in Table 2.

EXAMPLE 2

The procedure in Example 1 was repeated to carry out the oligomerization reaction except that the liquid which had been composed principally of cyclohexane and obtained as the overhead in the second distillation column was not treated with molecular sieve, but was used as such upon catalyst preparation and as the reaction solvent. The reaction conditions and performance results are given in Table 2.

COMPARATIVE EXAMPLE 1

The procedure in Example 1 was repeated to carry out the oligomerization reaction except that the liquid which had been composed principally of cyclohexane and obtained as the overhead in the second distillation column was incorporated with water so that the water concentration in the liquid was regulated to 15 ppm by wright, and was used upon catalyst preparation and as the reaction solvent. The reaction conditions and performance results are given in Table 2.

TABLE 2

|  | Example | | Compara- |
|---|---|---|---|
|  | 1 | 2 | tive Exp. 1 |
| Water concentration in solvent(wt-ppm) | ≦1 | 8 | 15 |
| Catalytic activity (g-oligomer/g-ZrCl$_4$/hour) | 7200 | 7000 | 5000 |

EXAMPLE 3

The procedure in Example 1 was repeated to carry out the catalyst preparation, oligomerization reaction, deactivation treatment of catalyst and distillation operation. The chemical composition of the overhead obtained in the second distillation column in the final distillation operation is given in Table 3, wherein the concentration of olefin having C-3 or more was 0.33% by weight. The distillation operation was carried out by the use of the equipment as illustrated in FIG. 5.

Subsequently, the procedure in Example 1 was repeated to carry out the [Oligomerization reaction] except that the liquid which had been composed principally of cyclohexane and obtained from the overhead of the second distillation column was used as the reaction solvent. As a result, the product distribution were comparable to those as given in Table 1. In Table 4 is given the purity of C-18, which is the production ratio of 1-octadecene as the objective product to the total production amount of C-18 and catalytic activity.

EXAMPLES 4 AND 5 AND REFERENCE EXAMPLE 1

The procedure in Example 3 was repeated to carry out Examples 4 and 5 and Reference Example 1 except that the distillation conditions as given in Table 5 were applied in place of those in Example 3. As a result, the product distribution were comparable to those as given in Table 1. The chemical composition of the overhead obtained in the second distillation column is given in Table 3. Further, in Table 4 is given the purity of C-18 and the catalytic activity in the case where the oligomerization reaction was put into practice by using as the reaction solvent, the liquid which had been composed principally of cyclohexane and obtained from the overhead of the second distillation column.

REFERENCE EXAMPLE 2

The procedure in Example 3 was repeated to carry out the oligomerization reaction except that the liquid which had been composed principally of cyclohexane and obtained as the overhead in the second distillation column was incorporated with water so that the water concentration in the liquid was regulated to 15 ppm by wright, and was recyclingly used. The results are given in Table 4.

COMPARATIVE EXAMPLE 2

The procedure in Reference Example 1 was repeated to carry out the oligomerization reaction except that the liquid which had been composed principally of cyclohexane and obtained as the overhead in the second distillation column was incorporated with water so that the water concentration in the liquid was regulated to 15 ppm by wright, and was recyclingly used. The results are given in Table 4.

TABLE 3

| Overhead liquid composition in | Example No. | | | Reference |
|---|---|---|---|---|
| 2nd distillation column (wt. %) | 3 | 4 | 5 | Example 1 |
| C-4 olefin | 0.18 | 0.39 | 0.95 | 2.47 |
| C-8 olefin | 0.15 | 0.28 | 0.79 | 3.12 |
| Cyclohexane | 99.67 | 99.33 | 98.26 | 94.41 |
| C-3 and more olefin | 0.33 | 0.67 | 1.74 | 5.59 |
| Water (ppm by wt) | 5 | 6 | 5 | 5 |

TABLE 4

|  | Example No. | | | Ref. | Ref. | Comp. |
|---|---|---|---|---|---|---|
|  | 3 | 4 | 5 | Ex. 1 | Ex. 2 | Ex. 2 |
| C-18 purity (wt %) | 94.4 | 94.3 | 94.1 | 92.6 | 95.8 | 94.5 |
| Catalytic activity (kg/g-ZrCl$_4$) | 12.5 | 12.6 | 12.6 | 12.5 | 9.0 | 9.1 |

{Remarks} Ref. Ex.: Reference Example
Comp. Ex.: Comparative Example

TABLE 5

|  | Example No. | | | Ref. | Ref. | Comp. |
|---|---|---|---|---|---|---|
|  | 3 | 4 | 5 | Ex. 1 | Ex. 2 | Ex. 2 |
| 1st Distillation Tower | | | | | | |
| Top temperature (° C.) | 66.1 | 63.8 | 60.1 | 56.0 | 66.1 | 56.0 |
| Bottom temperature (° C.) | 90.7 | 90.2 | 89.7 | 89.1 | 90.7 | 89.1 |
| Reflux ratio | 5 | 5 | 5 | 5 | 5 | 5 |
| Top flow rate (g/hour) | 47 | 38 | 28 | 20 | 47 | 20 |
| Bottom flow rate (g/hour) | 313 | 322 | 332 | 340 | 313 | 340 |
| 2nd Distillation Tower | | | | | | |
| Top temperature (° C.) | 80.0 | 80.0 | 79.9 | 79.9 | 80.0 | 79.9 |
| Bottom temperature (° C.) | 170.9 | 171.1 | 172.2 | 178.2 | 170.9 | 178.2 |
| Reflux ratio | 5 | 5 | 5 | 2 | 5 | 2 |
| Top flow rate (g/hour) | 170 | 179 | 190 | 202 | 170 | 202 |
| Bottom flow rate (g/hour) | 143 | 143 | 142 | 138 | 143 | 138 |

INDUSTRIAL APPLICABILITY

The present invention relates to a process for producing an ethylenic oligomer which is capable of producing a high quality ethylenic oligomer having enhanced purity, and in which a Ziegler based catalyst can maintain a high catalytic activity, when producing an ethylenic oligomer which is useful as a starting material for high molecular polymers, plasticizers, surfactants and the like by the use of the foregoing catalyst.

What is claimed is:

1. A process for producing an ethylenic oligomer which comprises subjecting ethylene to oligomerization reaction in an organic solvent in the presence of a Ziegler based catalyst, and recyclingly using for the oligomerization reaction, the organic solvent separated by distillng the resultant oligomerization reaction product, wherein the water concentration in the oligomerization reaction system is at most 8 ppm by weight.

2. A process for producing an ethylenic oligomer which comprises subjecting ethylene to oligomerization reaction in an organic solvent in the presence of a Ziegler based catalyst, and recyclingly using for the oligomerization reaction, the organic solvent separated by distillng the resultant oligomerization reaction product, wherein the water concentration in the organic solvent to be recycled in the oligomerization reaction system is at most 8 ppm by weight.

3. The process for producing an ethylenic oligomer according to claim 2, wherein the water concentration in the organic solvent is at most 5 ppm by weight.

4. The process for producing an ethylenic oligomer according to claim 1, wherein the organic solvent is selected from alicyclic compounds, aliphatic hydrocarbons, aromatic hydrocarbons and halogenated aliphatic hydrocarbons.

5. The process for producing an ethylenic oligomer according to claim 1, wherein the Ziegler based catalyst contains Zr.

6. The process for producing an ethylenic oligomer according to claim 1, wherein the concentration of olefins which have at least 3 carbon atoms and which are contained in the organic solvent to be recycled in the oligomerization reaction system is at most 2% by weight.

7. A process for producing an ethylenic oligomer which comprises subjecting ethylene to oligomerization reaction in an organic solvent in the presence of a Ziegler based catalyst, and recyclingly using for the oligomerization reaction, the organic solvent separated by distillng the resultant oligomerization reaction product, wherein the concentration of olefins which have at least 3 carbon atoms and which are contained in the organic solvent to be recycled in the oligomerization reaction system is at most 2% by weight.

8. The process for producing an ethylenic oligomer according to claim 7, wherein the organic solvent is selected from alicyclic compounds, aliphatic hydrocarbons, aromatic hydrocarbons and halogenated aliphatic hydrocarbons.

9. The process for producing an ethylenic oligomer according to claim 7, wherein the Ziegler based catalyst contains Zr.

10. The process for producing an ethylenic oligomer according to claim 7, wherein the olefins which have at least 3 carbon atoms are olefins which have 4 to 8 carbon atoms.

11. The process for producing an ethylenic oligomer according to claim 7, wherein the water concentration in the organic solvent to be recycled in the oligomerization reaction system is at most 8 ppm by weight.

12. The process for producing an ethylenic oligomer according to claim 2, wherein the organic solvent is selected from alicyclic compounds, aliphatic hydrocarbons, aromatic hydrocarbons and halogenated aliphatic hydrocarbons.

13. The process for producing an ethylenic oligomer according to claim 2, wherein the Ziegler based catalyst contains Zr.

14. The process for producing an ethylenic oligomer according to claim 2, wherein the concentration of olefins which have at least 3 carbon atoms and which are contained in the organic solvent to be recycled in the oligomerization reaction system is at most 2% by weight.

* * * * *